United States Patent [19]
Gaylord, Jr.

[11] 4,090,508
[45] May 23, 1978

[54] ORTHOPEDIC KNEE BRACE

[75] Inventor: John F. Gaylord, Jr., Matthews, N.C.

[73] Assignee: Medical Specialties, Incorporated, Charlotte, N.C.

[21] Appl. No.: 777,686

[22] Filed: Mar. 15, 1977

[51] Int. Cl.² .......................... A61F 5/01; A61F 13/06
[52] U.S. Cl. .................................... 128/80 C; 128/165
[58] Field of Search ................... 128/80 C, 165, 87 R, 128/82; 2/22, 24

[56] References Cited

U.S. PATENT DOCUMENTS

| | | | |
|---|---|---|---|
| 3,473,527 | 10/1969 | Spiro | 128/80 C |
| 3,804,084 | 4/1974 | Lehman | 128/80 C |
| 3,853,123 | 12/1974 | Moore | 128/80 C |
| 3,935,858 | 2/1976 | Harroff | 128/80 C |

*Primary Examiner*—John D. Yasko
*Attorney, Agent, or Firm*—Bell, Seltzer, Park & Gibson

[57] ABSTRACT

An orthopedic knee brace which is able to be adjustably sized in both length and circumference. The brace comprises a sheet of flexible material which is adapted to encircle the knee and adjacent leg portions of the wearer, and three rigidifying members are mounted on the sheet and extend between the upper and lower end edges thereof. The rigidifying members are each adapted to be readily shortened by the physician or the user, such that the sheet may be severed along the upper and/or lower end edges of the sheet, as well as along the side edges thereof, to selectively reduce both the length and circumference of the brace and thereby permit the brace to be properly fitted to patients of varying size.

19 Claims, 12 Drawing Figures

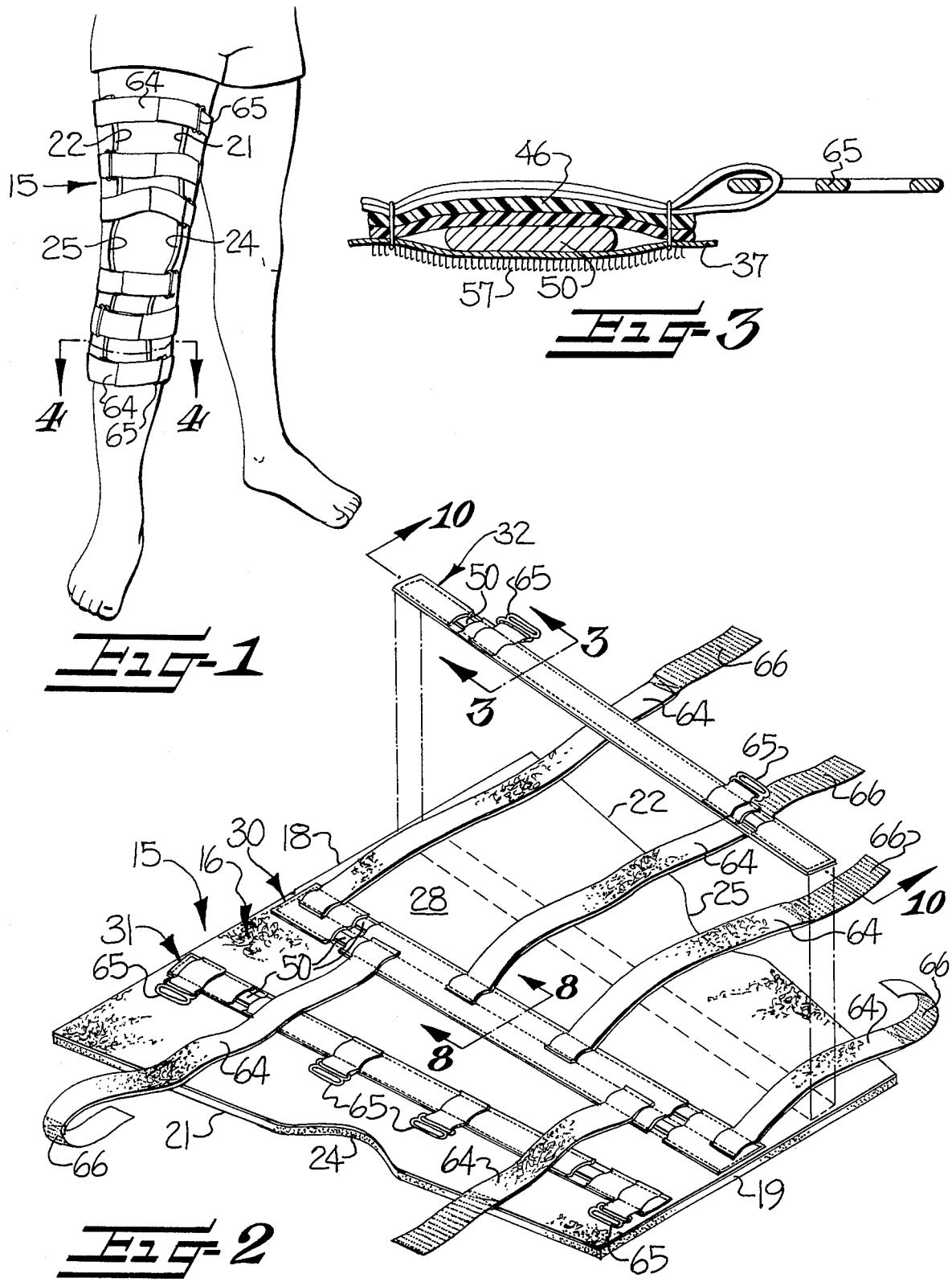

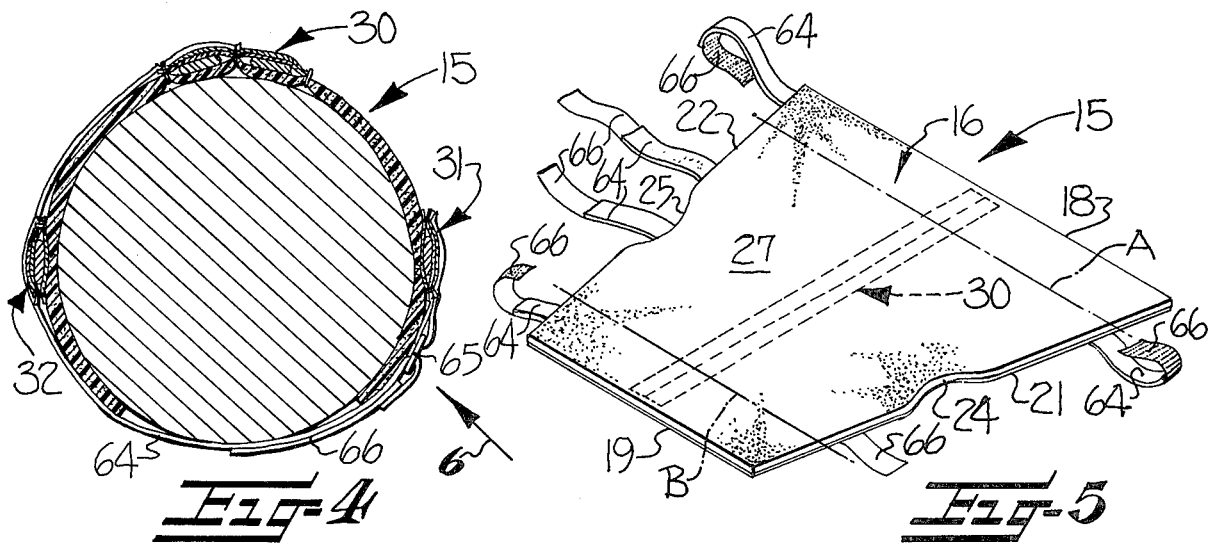
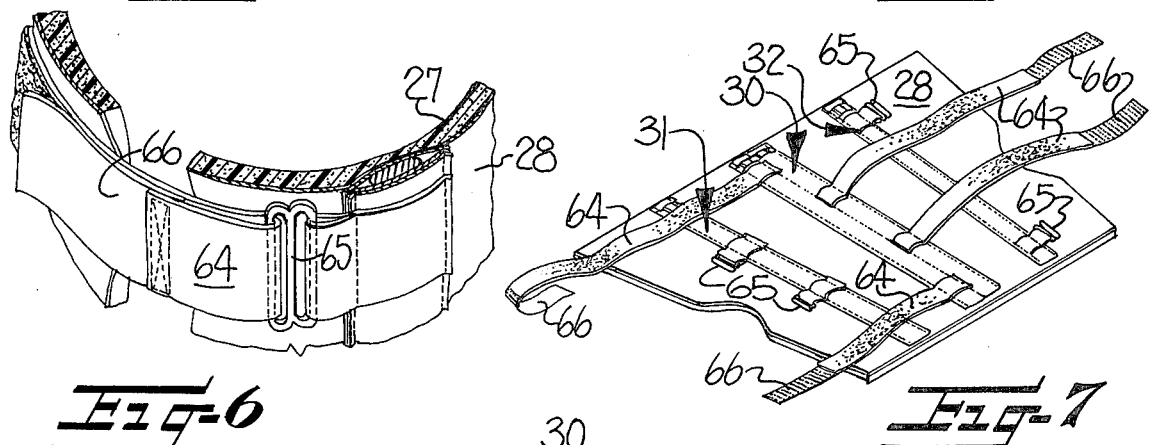
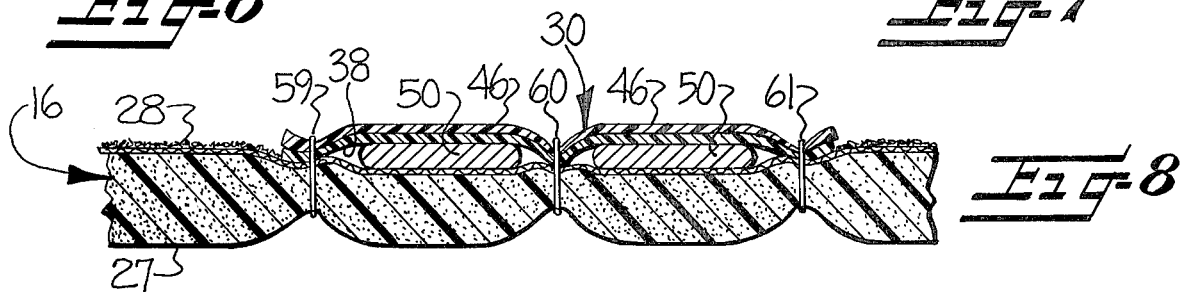
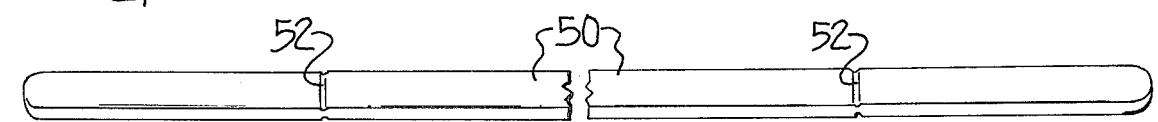
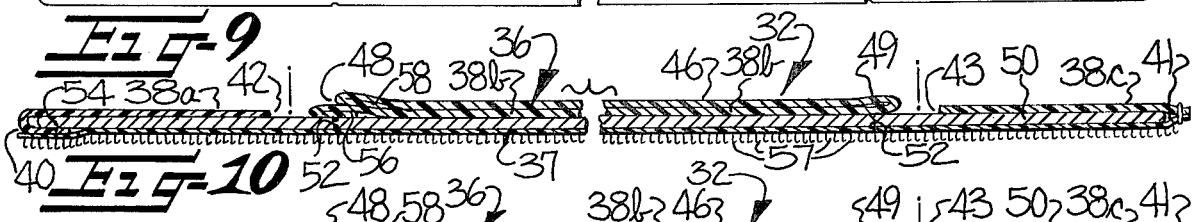
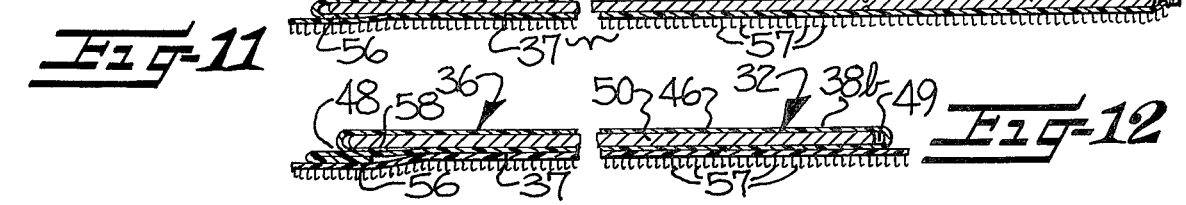
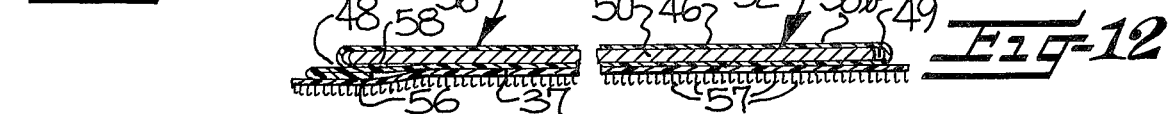

ORTHOPEDIC KNEE BRACE

The present invention relates to an orthopedic knee brace characterized by adjustability in both the length and circumferential directions so that the brace may be properly fitted to patients of varying size.

Orthopedic knee braces of various designs have heretofore been proposed for restraining the knee against normal bending movement. One such prior brace is shown in the U.S. patent to Harroff, No. 3,935,858. This prior brace comprises a flexible cover which is adapted to extend around the knee, a pair of rigidifying stays which are removably applied to the cover by "Velcro" fastening means, and a number of straps and associated rings attached to the removable rigidifying stays to secure the cover about the knee. It is stated in the patent that the brace is able to accommodate patients of varying size.

While the above Harroff brace does provide a degree of adjustability in the circumferential direction, it is unable to provide adjustability in the lengthwise direction since the rigidifying stays may not be readily shortened. Thus the ability to fit the brace to patients of varying size is seen to be severely limited. In addition, the adjustable stays of the Harroff patent are subject to inadvertent release, particularly when the binding straps are secured thereto in the manner illustrated in the patent, since the binding straps tend to pull against and release the rigidifying stays when the straps are tightened about the knee.

It is accordingly an object of the present invention to provide an orthopedic knee brace which is adjustable in both the length and circumferential directions.

It is another object of the present invention to provide an orthopedic knee brace having rigidifying members which may be readily severed by the physician or user, to thereby permit the length of the brace to be selectively shortened.

It is a further object of the present invention to provide an orthopedic knee brace having readily severable rigidifying members, and which has provision for protectively covering both ends of the severed metal stays of the rigidifying members after the shortening thereof.

It is also an object of the present invention to provide a knee brace of the described type and which includes removable side rigidifying members to permit the adjustable placement thereof with respect to the knee of the wearer, and wherein the removable side rigidifying members are held in the desired operative position by the circumferential binding straps and are not subject to inadvertent release.

These and other objects and advantages of the present invention are achieved in the embodiment illustrated herein by the provision of an orthopedic knee brace which comprises a sheet of readily severable material which is adapted to encircle the knee and adjacent leg portions of the patient, and a rigidifying member attached to the sheet and extending between the upper and lower end edges thereof. The rigidifying member preferably comprises an elongate encasement having a relatively rigid stay removably disposed therein.

The rigidifying member of the present invention is adapted to be readily severed by the physician or user to permit its lengthwise adjustment, and in this regard, the encasement comprises first and second overlying strips which define a first pocket therebetween and which has an open end and a closed end. Preferably, the second or outer strip is discontinuous adjacent one of its ends to define an interruption, and the stay comprises a frangible material having a transverse score line thereon which is positioned at a point which generally conforms to the position of the interruption when the stay is positioned in the first pocket. Thus the length of the brace may be shortened by initially removing the stay from the first pocket of the encasement, severing the sheet material and encasement along a line which extends through the interruption of the second strip, shortening the length of the stay to conform to the length of the remaining portion of the pocket by manually breaking the same at the score line, and then positioning the shortened stay in the remaining portion of the pocket.

In the preferred embodiment of the invention, the second strip includes an interruption adjacent each of its ends. In addition, a third strip overlies substantially the full length of that portion of the second strip lying between the interruptions to define a second pocket therebetween which also has an open end and a closed end. By this arrangement, the brace may be selectively shortened to a first reduced length by severing the brace through one of the interruptions in the manner described above, or shortened to a second further reduced length by removing the stay from the first pocket, severing the sheet material and encasement along a pair of parallel lines such that one line passes through each interruption, shortening the length of the stay to conform to the length of said second pocket, and inserting the shortened stay into the second pocket. The encasement may also include flap means to protectively cover the end of the stay in each of the length configurations of the rigidifying member.

The knee brace of the present invention preferably includes three separate rigidifying members, with one of the members being fixedly attached to the central portion of the sheet, and two side members being removably attached to the sheet so that the side members may be properly disposed along each side of the patient's knee when the brace is operatively positioned thereabout. The sheet is adapted to be bound in encircling relation about the knee by a plurality of laterally directed straps and associated buckles. The straps are preferably attached to the centrally disposed rigidifying members, and the buckles are attached to the removable side rigidifying members, such that each strap is adapted to substantially encircle the leg of the patient to engage the cooperaring buckle and thereby overlie one of the removable rigidifying members and bind the member to the sheet. Also, this construction results in the lateral force which is exerted upon the removable rigidifying members by the straps being substantially reduced as compared to the Harroff structure, to thereby further reduce the likelihood of the inadvertent release of the rigidifying members.

Some of the objects having been stated, other objects will appear as the description proceeds, when taken in connection with the accompanying drawings, in which FIG. 1 is a perspective view of an orthopedic knee brace which embodies the features of the present invention, and illustrating the brace in operative position encircling the knee and adjacent leg portions of a patient;

FIG. 2 is a perspective view of the brace in a planar configuration, and further illustrating the manner in which the side rigidifying members are removably attached to the sheet of the brace;

FIG. 3 is a sectional view of the rigidifying member of the brace taken substantially along the line 3—3 of FIG. 2;

FIG. 4 is a sectional plan view of the brace taken substantially along the line 4—4 of FIG. 1;

FIG. 5 is a perspective view of the brace in planar configuration, and illustrating the opposite side from that seen in FIG. 2;

FIG. 6 is a fragmentary perspective view illustrating the strap means of the brace for circumferentially binding the sheet in encircling relation about the knee;

FIG. 7 is a view of the brace similar to FIG. 2, but illustrating the same after the length has been shortened by removing a portion thereof along each of the upper and lower end edges;

FIG. 8 is a sectional view of the centrally positioned rigidifying member and taken substantially along the line 8—8 of FIG. 2;

FIG. 9 is a perspective view of the metal stay used in the rigidifying member of the knee brace of the present invention;

FIG. 10 is a sectional elevation view of the rigidifying member, and taken substantially along the line 10—10 of FIG. 2;

FIG. 11 is a view similar to FIG. 10, but illustrating the rigidifying member after one end portion has been removed therefrom; and FIG. 12 is a view similar to FIG. 10, but illustrating the rigidifying member after both end portions have been removed, and with the stay positioned in the second pocket.

Referring more specifically to the drawings, there is illustrated an orthopedic knee brace 15 which embodies the present invention, and which comprises a sheet 16 of readily severable flexible material having parallel upper and lower end edges 18 and 19 respectively, and opposite side edges 21 and 22. The side edges are somewhat inclined with respect to each other, to result in an overall trapezoidal configuration when the sheet is disposed in a planar configuration as seen in FIG. 2. Also, the side edges 21, 22 each include an indentation 24 and 25 respectively, for accommodating the kneecap when the brace is operatively positioned to encircle the knee and adjacent leg portions of the patient in the manner shown in FIG. 1.

In the illustrated embodiment, the sheet 16 is a laminate which comprises an inner layer 27 of foam material and an outer layer 28 of fabric material which is bonded in superposed relation to the foam. The foam typically comprises an open cell polyurethane foam having a thickness of about 5/16 inches, and the fabric 28 may for example comprise a tightly knit nylon material which is napped to result in myriad upstanding and relatively free fiber loops on the outer surface thereof.

The brace 15 further includes three rigidifying members 30, 31 and 32 disposed to extend between the upper and lower end edges of the brace. As best seen in FIG. 2, the rigidifying member 30 is centrally disposed on the sheet midway between the side edges 21, 22, and so as to extend between the upper and lower end edges. The member 30 is fixedly attached to the sheet by stitching or the like, and as will be apparent, the member 30 is adapted to be positioned along the back of the knee when the brace is in its operative position. The two side rigidifying members 31, 32 are adapted to be removably attached to the sheet on each side of the centrally disposed member in the manner hereinafter further described.

The side rigidifying members 31 and 32 each comprise an elongate encasement 36 comprising an underlying or first continuous strip 37, and a second strip composed of three segments 38a, 38b, and 38c (collectively referred to herein as the strip 38) overlying substantially the full length of the underlying strip 37. The second strip 38 is attached to the underlying strip 37 by stitching to define a first pocket therebetween which has an open end 40 and a closed end 41. In addition, the second strip 38 is discontinuous at a point adjacent each of its ends to define the three segments 38a, 38b, and 38c, and a pair of interruptions 42, 43. A third strip 46 overlies substantially the full length of that portion of the second strip lying between the interruptions, i.e., the segment 38b, and the end portions of the second strip positioned outside of the interruptions, i.e., the segments 38a and 38c, are non-covered. The third strip is attached to the segment 38b by stitching to define a second pocket between the strips 38 and 46, and which also has an open end 48 and a closed end 49. As seen in FIG. 10, the open and closed ends of the two pockets are aligned, and preferably, the open ends will be positioned adjacent the upper end edge 18 of the sheet. Also, it will be seen that in the illustrated embodiment, the third strip 46 and the segment 38b of the second strip comprise a unitary member which is doubled upon itself to form the closed end 49 of the second pocket.

Each rigidifying member 31 and 32 further includes an elongate stay 50 having a length which generally corresponds to the length of the first pocket, such that the stay may be inserted and removed through the open end 40 thereof. As illustrated, the stay 50 is relatively flat and thin, and preferably is fabricated from a metallic material, such as aluminum, which may be bent within limits to permit the stay and rigidifying member to be shaped to follow the anatomy of the wearer, but which is sufficiently frangible to permit the stay to be broken if desired. In this regard, the stay 50 further includes a score line 52 adjacent each end to facilitate the manual breaking thereof at either one or both of the score lines. As best seen in FIGS. 9 and 10, each score line 52 comprises a pair of opposed notches in the stay, and the positioning of the score lines 52 on the stay is such that the score lines are positioned at points along the length of the stay which generally conform to the positioning of the interruptions 42, 43 along the length of the second strip of the encasement, but with the score lines being positioned slightly within the interruptions for the reason to become apparent, note FIG. 10.

The encasement of each rigidifying member 31 and 32 further includes flap means for protectively covering the end of the stay in each of the configurations of the rigidifying member as hereinafter further described. More particularly, the second strip includes a first flap 54 adjacent the open end 40 of the first pocket. As best seen in FIG. 10, the first flap 54 comprises a reversely directed extension which extends a relatively short distance into the open end 40 of the first pocket. A second flap 56 is carried by the segment 38b of the second strip adjacent the interruption 42 and which comprises a reversely directed extension of the second strip which extends a relatively short distance into the remaining portion of the first pocket. In addition, a third flap 58 is carried by the third strip 46 adjacent the open end 48 of the second pocket and which comprises an extension of the third strip which extends a relatively short distance into the open end 48 of the second pocket.

The two side members 31 and 32 are removably attached to the sheet 16 to permit these two members to be adjustably positioned along the sides of the knee when the brace is operatively positioned about the knee of the patient. In this regard, the means for removably attaching the side members 31 and 32 to the sheet comprises "Velcro" type hook means 57 carried by the underside of the strip 37. As well known in the art, such "Velcro" hook means is adapted to releasably engage the fibrous fabric material 28 of the sheet when the member is pressed into contact with the sheet, and the member may be removed therefrom by pulling the member from the sheet.

As best seen by a comparison of FIGS. 3 and 8, the centrally disposed rigidifying member 30 differs from the side rigidifying members 31, 32 in that it is fixedly attached to the sheet 16 by the lines of stitching 59, 60, and 61 (FIG. 8) so as to extend between the end edges 18 and 19 thereof. In addition, the underlying strip 37 is omitted, with the first pocket thus being formed between the overlying strip 38 and sheet 16. Also, the centrally disposed member 30 in effect comprises a pair of integrally connected side-by-side rigidifying members. More particularly, the member 30 is formed by the use of relatively wide strips 38 and 46, and with a central switch line 60 serving to divide the strips into like, side-by-side encasements, each otherwise having the structure as described above.

Means are also provided for circumferentially binding the sheet 16 in encircling relation about the knee of the patient, note FIG. 1. In particular, a plurality of straps 64 extend laterally and in opposite directions from the centrally disposed rigidifying member 30. A like number of cooperating fasteners in the form of buckles 65 are attached to the side rigidifying members 31 and 32, with the associated buckle of each strap being positioned on the rigidifying member which is disposed on the side of the central member 30 opposite from the direction in which the associated strap extends. Thus each strap 64 is adapted to substantially encircle the leg of the patient to engage its cooperating buckle 65. By this arrangement, a plurality of straps 64 overlie each side rigidifying member 31 and 32 to bind the same in operative position, and thereby prevent the members 31 and 32 from being pulled away from the fabric of the sheet by the lateral forces exerted on the buckles by the straps 64.

Each of the straps 64 includes a segment 66 of "Velcro" type hook means carried at the end thereof, and the remaining portion of the strap includes a fibrous fabric material of a type adapted to be releasably engaged by the hook means of the segment 66. Thus each strap 64 may be bound about the brace by threading the same through its associated buckle, and then reversely drawing the strap so that the hook means of the segment 66 may be attached to the remaining portion of the strap.

Viewing FIG. 2, it will be noted that one of the straps 64 is connected to each of those portions of the second strip of the central member which are outside of the interruptions 42, 43, and another of the straps is attached to the third strip 46 of the central member 30 immediately adjacent each of the interruptions. By this arrangement, a strap 64 is disposed along each of the upper and lower end edges of the brace in each of its length configurations as described below.

In accordance with the present invention, the length of the above described knee brace 15 may be selectively shortened to permit use by patients of varying size. In particular, the brace may be employed in its original length as shown in FIG. 2. Where the patient requires a somewhat shorter brace, the brace may be shortened to a first reduced length by initially removing the stays 50 from the first pocket of each encasement 36, severing the sheet material 16 and encasement 36 along a line A which extends in a direction parallel to the upper end edge 18 of the sheet and through the aligned interruptions 42 of the rigidifying members. The sheet material is readily severable, and may be easily cut by hand using a pair of conventional scissors. Each stay is then shortened by manually breaking the same at one of the score lines 52 such that its remaining length conforms to the length of the remaining portion of the first pocket. The shortened stay is then inserted into the remaining portion of the first pocket, and the end of the stay is covered by the second flap 56 which is manipulated to overlie the end of the stay, note FIG. 11. The flap 56 thus not only serves to effectively retain the stay in the second pocket, but also to prevent the end of the stay from coming into contact with the body of the wearer.

Where the brace 15 is to be fitted to a relatively small patient, it may be further shortened by removing each stay 50 from its original position in the first pocket, severing the sheet material 16 and each of the encasements 36 along a pair of parallel lines A and B which are parallel to the upper and lower end edges and which extend through the interruptions 42, 43 of the encasements. Each stay 50 is then shortened by manually breaking the same at both score lines 52. The remaining portion of the shortened stay is then inserted into the second pocket, and the end of the stay is protectively covered by the third flap 58, note FIG. 12. Thus the brace 15 of the present invention is selectively usable in any one of three distinct lengths. In addition, the circumference of the brace may be readily adjusted by cutting along one or both of the side edges 21, 22 of the sheet material. In this regard, the positioning of the indentations 24, 25 may be varied during the cutting operation to further enhance the conformability of the brace to the particular patient.

In the drawings and specification, there has been set forth a preferred embodiment of the invention, and although specific terms are employed, they are used in a generic and descriptive sense only and not for purposes of limitation.

That which is claimed is:

1. An orthopedic knee brace characterized by the ability to be adjusted in both length and circumference so that it may be properly fitted to patients of varying size, and comprising a sheet of readily severable flexible material having upper and lower end edges and opposite side edges, and being adapted to encircle the knee and adjacent leg portions of the patient, a rigidifying member having a length to extend substantially between the upper and lower end edges of said sheet and comprising (a) an elongate encasement comprising an underlying continuous strip, a second strip attached to and overlying substantially the full length of said underlying strip to define a first pocket therebetween which has an open end and a closed end, and a third strip attached to and overlying a substantial portion but not the full length of said second strip to define a non-covered portion of said second strip and to further define a second pocket between said second and third strips which has an open end and a closed end, and (b) a relatively rigid stay having a length generally corresponding to the length of said first pocket such that the stay may be inserted and removed through the open end thereof, means for attaching said rigidifying member to said flexible sheet so as to extend between said end edges of said sheet, and means for circumferentially binding said sheet in encircling relation about the knee and adjacent leg portions of the patient, whereby the length of the brace may be shortened by initially removing the stay from said first pocket of said encasement, severing the sheet material and encasement along a line which extends through said non-covered portion of said second strip, shortening the length of said stay to conform to the length of said second pocket, and then positioning the shortened stay in said second pocket by inserting the stay through the open end thereof.

2. The orthopedic knee brace as defined in claim 1 further comprising flap means carried by said second strip adjacent the open end of the first pocket for protectively covering the end of the stay when it is in said first pocket.

3. The orthopedic knee brace as defined in claim 2 wherein said encasement further comprises flap means carried by said third strip adjacent the open end of said second pocket for protectively covering the end of the stay when it is in said second pocket.

4. The orthopedic knee brace as defined in claim 3 wherein said stay comprises a frangible metallic material, and further includes a transverse score line at a predetermined location thereon to facilitate the manual breaking of the stay at the score line.

5. An orthopedic knee brace characterized by the ability to be adjusted in both length and circumference so that it may be properly fitted to patients of varying size, and comprising a sheet of readily severable flexible material having upper and lower end edges and opposite side edges, and being adapted to encircle the knee and adjacent leg portions of the patient, a rigidifying member having a length to extend substantially between the upper and lower edges of said sheet and comprising (a) an elongate encasement comprising an underlying continuous strip, a second strip attached to and overlying substantially the full length of said underlying strip to define a pocket therebetween which has an open end and a closed end, said second strip being discontinuous adjacent one of its ends to define an interruption, an end portion of the pocket on one side of said interruption, and a remaining portion of the pocket on the other side of said interruption, (b) a relatively rigid stay having a length generally corresponding to the length of said pocket such that the stay may be inserted and removed through the open end thereof, means for attaching said rigidifying member to said flexible sheet so as to extend between said end edges of said sheet, and means for circumferentially binding said sheet in encircling relation about the knee and adjacent leg portions of the patient, whereby the length of the brace may be shortened by initially removing the stay from said pocket of said encasement, severing the sheet material and encasement along a line which extends through said interruption of said second strip, shortening the length of said stay to conform to the length of remaining portion of said pocket, and then positioning the shortened stay in the remaining portion of said pocket.

6. The orthopedic knee brace as defined in claim 5 wherein said stay comprises a frangible material, and includes a transverse score line positioned at a point along its length which generally conforms to the positioning of said interruption along the length of said second strip, whereby the stay may be readily broken by hand at the score line and with the remaining portion of the stay approximately conforming to the length of the remaining portion of said pocket.

7. The orthopedic knee brace as defined in claim 5 wherein said encasement further comprises first flap means carried by said second strip adjacent the open end of said pocket and which comprises an extension of said second strip which is adapted to reversely extend a relatively short distance into the open end of said pocket, and thereby protectively cover the end of said stay when the stay is positioned in said pocket.

8. The orthopedic knee brace as defined in claim 7 wherein said encasement further comprises second flap means carried by said second strip adjacent said interruption and which comprises an extension of said second strip which is adapted to reversely extend a relatively short distance into the remaining portion of the pocket and thereby protectively cover the end of said stay when the stay is positioned in the remaining portion of the pocket.

9. An orthopedic knee brace characterized by the ability to be adjusted in both length and circumference so that it may be properly fitted to patients of varying size, and comprising a sheet of readily severable flexible material having parallel upper and lower end edges and opposite side edges, and being adapted to encircle the knee and adjacent leg portions of the patient, a plurality of rigidifying members, each having a length to extend substantially between the upper and lower end edges of said sheet and each comprising (a) an elongate encasement comprising an underlying continuous strip, a second strip attached to and overlying substantially the full length of said underlying strip to define a first pocket therebetween which has an open end and a closed end, said second strip being discontinuous adjacent each of its ends to define a pair of interruptions, and a third strip attached to and overlying substantially the full length of that portion of said second strip lying between said interruptions to define a second pocket therebetween which has an open end and a closed end, and (b) a relatively rigid stay having a length generally corresponding to the length of said first pocket such that the stay may be inserted and removed through the open end thereof, means for attaching each of said rigidifying members to said flexible sheet so as to extend between said end edges of said sheet, and means for circumferentially binding said sheet in encircling relation about the knee and adjacent leg portions of the patient, whereby the length of the brace may be shortened to a first reduced length by initially removing the stay from said first pocket of said encasement, severing the sheet material and encasement along a line which extends through the interruption of said second strip which is adjacent the open end of said first pocket, shortening the length of said stay to conform to the length of the remaining portion of said first pocket, and inserting the shortened stay into the remaining portion of said first pocket; or to a second reduced length by initially removing the stay from said first pocket, severing the sheet material and encasement along a pair of parallel lines such that a line passes through each interruption, shortening the length of said stay to conform to the length of said second pocket, and inserting the shortened stay into said second pocket.

10. The orthopedic knee brace as defined in claim 9 wherein there are a pair of said rigidifying members, and said means for attaching each of said rigidifying members to said flexible sheet comprises means for removably attaching each of said rigidifying members to said sheet to permit the rigidifying members to be adjustably positioned along the sides of the knee when the brace is operatively worn by the patient.

11. The orthopedic knee brace as defined in claim 10 wherein said sheet of flexible material comprises a fibrous fabric material, and said means for removably attaching each of said side rigidifying members to said sheet comprises hook means carried by said underlying strip of said encasement for releasably engaging said fibrous fabric material.

12. The orthopedic knee brace as defined in claim 11 wherein said sheet of flexible material further comprises a layer of flexible foam material bonded to the side of said fabric material opposite said rigidifying members.

13. The orthopedic knee brace as defined in claim 11 further comprising a third rigidifying member fixedly mounted to said sheet and extending between said upper and lower end edges at a central location on said sheet so as to be adapted to be positioned along the back of the knee of the patient, said third rigidifying member comprising an elongate overlying strip attached to said sheet to define a first pocket between said overlying strip and sheet which has an open end and a closed end, said overlying strip being discontinuous adjacent each of its ends to define a pair of interruptions, and a further strip attached to and overlying substantially the full length of that portion of said overlying strip lying between said interruptions to define a second pocket therebetween which has an open end and a closed end, and a relatively rigid stay having a length generally corresponding to the length of said first pocket such that the stay may be inserted and removed through the open end thereof.

14. The orthopedic knee brace as defined in claim 13 wherein said interruptions in said pair of side rigidifying members and said third rigidifying member are laterally aligned when said side rigidifying members are operatively positioned on said sheet.

15. The orthopedic knee brace as defined in claim 13 wherein said means for circumferentially binding the sheet in encircling relation about the knee of a patient comprises a plurality of straps attached to said third rigidifying member and extending laterally and in opposite directions therefrom, and a like number of cooperating fasteners attached to said pair of side rigidifying members, and wherein each strap is adapted to substantially encircle the leg of the patient and engage a cooperating fastener, and such that the straps each overlie one of the side rigidifying members to bind the same to said sheet.

16. The orthopedic knee brace as defined in claim 15 wherein one of said straps is connected to each of the portions of said overlying strip of said third rigidifying member outside of said interruptions, and another of said straps is attached to said further strip immediately adjacent each of said interruptions, whereby a strap is disposed along each of the upper and lower end edges of said sheet in each of the size configurations thereof.

17. The orthopedic knee brace as defined in claim 9 wherein the open and closed ends of said first and second pockets of each of said rigidifying members are aligned.

18. An orthopedic knee brace characterized by the ability to be adjusted in both length and circumference so that it may be properly fitted to patients of varying size, and comprising a sheet of readily several flexible material having upper and lower end edges and opposite side edges, and being adapted to encircle the knee and adjacent leg portions of the patient, a rigidifying member fixedly mounted to said sheet and extending substantially between the upper and lower end edges of said sheet and comprising (a) an elongate overlying strip attached to said sheet to define a first pocket therebetween which has an open end and a closed end, and a further strip attached to and covering a substantial portion but not the full length of said overlying strip to define a non-covered portion of said overlying strip and to further define a second pocket between said overlying and further strips which has an open end and a closed end, and (b) a relatively rigid stay having a length generally corresponding to the length of said first pocket such that the stay may be inserted and removed through the open end thereof, means for circumferentially binding said sheet in encircling relation about the knee and adjacent leg portions of the patient, whereby the length of the brace may be shortened by initially removing the stay from said first pocket, severing the sheet material and overlying strip along a line which extends through said non-covered portion of said overlying strip, shortening the length of said stay to conform to the length of said second pocket, and then positioning the shortened stay in said second pocket by inserting the stay through the open end thereof.

19. The orthopedic knee brace as defined in claim 18 wherein said overlying strip is discontinuous adjacent each of its ends to define a pair of interruptions, and said further strip covers substantially the full length of that portion of said overlying strip lying between said interruptions.

* * * * *